United States Patent [19]

Bonfield et al.

[11] Patent Number: 4,473,712

[45] Date of Patent: Sep. 25, 1984

[54] PURIFICATION OF CRUDE HEXAFLUOROACETONE CONTAINING NITROGEN OXIDES AND SULFUR DIOXIDE

[75] Inventors: John H. Bonfield, Somerset County, N.J.; Bela I. Karsay, Onondaga, N.Y.

[73] Assignee: Allied Corporation, Morris Township, Morris County, N.J.

[21] Appl. No.: 509,470

[22] Filed: Jun. 30, 1983

[51] Int. Cl.³ ............................................. C07C 45/80
[52] U.S. Cl. .................................................. 568/411
[58] Field of Search ................................ 568/410, 411

[56] References Cited

U.S. PATENT DOCUMENTS

| | | | |
|---|---|---|---|
| 3,433,838 | 3/1969 | Cunningham et al. | 260/593 |
| 3,544,633 | 12/1970 | Yodis et al. | 260/593 |
| 3,745,093 | 7/1973 | Lee | 203/49 |
| 4,337,361 | 6/1982 | Anello et al. | 568/386 |

*Primary Examiner*—James H. Reamer
*Attorney, Agent, or Firm*—Alan M. Doernberg; Gerhard H. Fuchs; Kenneth E. Stroup, Jr.

[57] ABSTRACT

Crude hexafluoroacetone containing as impurities nitrogen oxides and sulfur dioxide is purified by admixing with water to form an aqueous solution, admixing the aqueous solution with concentrated sulfuric acid or oleum to form a vapor and scrubbing the vapor with liquid concentrated sulfuric acid to produce purified anhydrous hexafluoroacetone. The sulfur dioxide and nitrogen oxides interact with the aqueous solution and concentrated sulfuric acid so as not to be found in the purified product, thus obviating the need for a neutralization step.

9 Claims, 1 Drawing Figure

U.S. Patent  Sep. 25, 1984  4,473,712
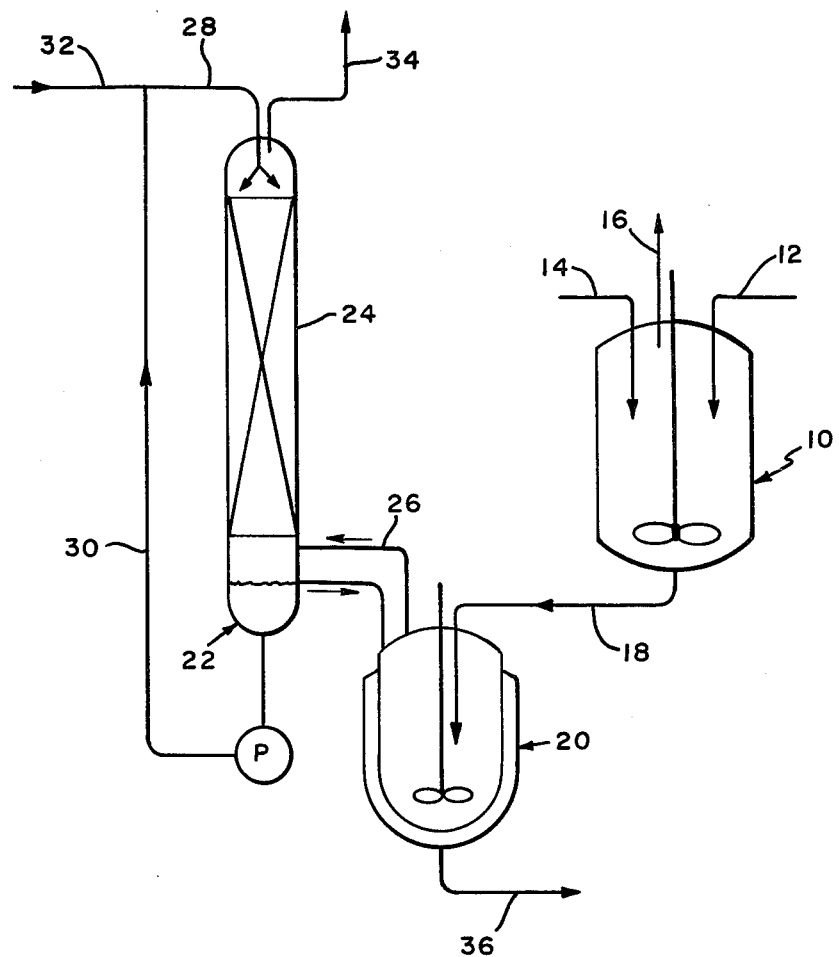

PURIFICATION OF CRUDE HEXAFLUOROACETONE CONTAINING NITROGEN OXIDES AND SULFUR DIOXIDE

The present invention relates to the purification of crude hexafluoroacetone, and especially to such purification when the impurities include nitrogen oxides and sulfur dioxide.

Hexafluoroacetone (also known as HFA or 6FK) has been produced by a variety of processes to be used as a reagent in Friedel-Crafts reactions, telomerization reactions and secondary conversion reactions. For these applications, 6FK of high purity and dryness is required.

Some processes for producing 6FK react HF with hexachloroacetone, to produce a product contaminated with HCl, HF and partially fluorinated acetones such as monochloropentafluoroacetone and dichlorotetrafluoroacetone. A variety of purification schemes have been proposed using distillation (Dupont's U.S. Pat. No. 3,745,093 to Lee (1973)) or absorption in water to form the 6FK monohydrate, dihydrate and trihydrate. In FIG. 1 and Example 1 of U.S. Pat. No. 3,544,633 to Yodis et al (1970), the trihydrate is formed and deabsorbed of volatiles; the trihydrate is dehydrated with sulfur trioxide and sulfuric acid; the dehydrated product is neutralized with sodium carbonate; and the neutralized product is again dehydrated with sulfur trioxide and sulfuric acid. In FIG. 3 and Example 3 of U.S. Pat. No. 3,544,633, the dihydrate is formed, neutralized with sodium bicarbonate, filtered and dissociated to form 6FK and 6FK trihydrate. The 6FK is dried by passage through 98% sulfuric acid, while the 6FK trihydrate is recycled to absorb more crude product and form the dihydrate. See also U.S. Pat. No. 3,433,838 of Cunningham et al. (1969).

Other processes for producing 6FK proceed from hexafluorothioacetone (HFTA), usually present as its dimer, via oxidation to 6FK and sulfur, distilling off crude 6FK. Impurities in such a crude produce will include sulfur dioxide and the oxidant, if volatile. In the process of U.S. Pat. No. 4,337,361 of Anello et al. (1982), the oxidant can be nitrogen oxides such as NO or $NO_2$, collectively referred to as $NO_x$. Accordingly, 6FK vapor is produced containing sulfur dioxide and $NO_x$ as impurities.

BRIEF DESCRIPTION OF THE INVENTION

The present invention includes a process for the purification of crude hexafluoroacetone, containing as impurities nitrogen oxides and sulfur dioxide, which process comprises the steps:

(a) admixing the crude hexafluoroacetone with sufficient water at a temperature between about 40° C. and about 70° C. to produce an aqueous solution containing between about 70 and about 85 weight percent hexafluoroacetone, based upon weight of hexafluoroacetone and water, (b) admixing the aqueous solution with concentrated sulfuric acid or oleum at a temperature of at least about 90° C. in an amount sufficient to produce a liquid containing sulfuric acid at a concentration of at least about 70% (by weight of $H_2SO_4$ divided by $H_2SO_4$ plus water) and a vapor consisting essentially of hexafluoroacetone and hexafluoroacetone monohydrate, and (c) scrubbing said vapor consisting essentially of hexafluoroacetone and hexafluoroacetone monohydrate with liquid concentrated sulfuric acid at a flow rate sufficient to produce purified anhydrous hexafluoroacetone as a vapor of at least 99% purity.

DETAILED DESCRIPTION OF THE INVENTION

The process of the present invention is particularly applicable to the crude 6FK produced by the process of U.S. Pat. No. 4,337,361 using $NO_x$ as the oxidant. However, other processes producing 6FK containing sulfur dioxide and at least one nitrogen oxide, as impurities, may suitably be purified by the present process. Other impurities and especially non-condensible impurities, may be present without harm. Furthermore, impurities which absorb in water, but which also absorb in concentrated sulfuric acid, may be present in the crude hexafluoroacetone purified by the present process, which impurities will not be found in the purified hexafluoroacetone.

A common range of impurities in the crude hexafluoroacetone is between about 2 and about 6 weight percent sulfur dioxide and between about 1 and about 2 weight percent nitrogen oxides. It is convenient to disregard the non-condensible impurities which may also be present, such as oxygen, nitrogen and noble gases, all of which may be present if air is introduced during the HFTA oxidation, or when the $NO_x$ is generated from air without condensation therefrom.

The first step of the present process is to admix (absorb) the crude hexafluoroacetone with water. The temperature of this absorption should be between about 40° C. and about 70° C., preferably between about 50° C. and about 60° C., in order to insure a maximum absorption rate and a minimum contamination of hexafluoroacetone in the vent gases. Under those conditions, impurities such as oxygen and nitrogen will pass through the liquid phase, while hexafluoroacetone will be completely absorbed. If the absorption is done on a batch basis, absorption should continue until the hexafluoroacetone concentration is between about 70 and about 85 weight percent, based upon total weight of hexafluoroacetone in water. In semicontinuous operations (e.g., with counterflowing crude hexafluoroacetone and water streams), the contact times and flow rates can be adjusted to achieve similar levels. If one considers the 6FK and water only, then a concentration of 75.45 weight percent 6FK corresponds to 6FK trihydrate; a concentration of 82.2% 6FK corresponds to 6FK dihydrate; and a concentration of 90.2% 6FK corresponds to 6FK monohydrate. In order to achieve rapid absorption of 6FK into the liquid phase, without forming precipitates of 6FK monohydrate, final concentrations between about 70 and about 85 weight percent hexafluoroacetone have been chosen. It is preferred, however, that this concentration be between about 72 and about 82 weight percent hexafluoroacetone, since levels below 72% will contain unnecessary excess water (consuming sulfuric acid later as described below), while levels above 82% will have less water present than the dihydrate, and accordingly have the potential of leading to monohydrate precipitation. In one form of the invention wherein the 6FK trihydrate is to be distilled from the aqueous solution form, initial concentrations between about 72 and about 76 weight percent hexafluoroacetone are preferred, since, with these concentrations, heating will not generate anhydrous 6FK, which is formed by decomposition of the dihydrate and has a boiling point substantially lower than that of the trihydrate.

In the process of the present invention, unlike many of the processes of U.S. Pat. Nos. 3,544,633 and 3,433,838, the aqueous solution formed by absorption may be dehydrated directly to produce the purified hexafluoroacetone. In particular, it is unnecessary in most cases to neutralize acidic impurities, to filter or to conduct either a dehydration or a desorption step. It is contemplated, however, that in particular forms of the invention, a desorption step at a temperature between about 90° C. and about 140° C. may be conducted. In particular, when the aqueous solutions contains 6FK at a concentration between about 72 and about 76 weight percent hexafluoroacetone, heating to reflux boil will not cause substantial vapor pressures of 6FK or any of its hydrates to form, but will remove certain impurities such as sulfur dioxide and carbon dioxide, which impurities have a higher vapor pressure (lower solubility) at this temperature compared to the absorption temperature. It is also contemplated, especially when the aqueous solution contains between about 72 and about 76 weight percent hexafluoroacetone, to then distill hexafluoroacetone (as a trihydrate) from the aqueous solution, leaving behind such non-volatile residual materials as may be present, having been formed during the absorption step.

The aqueous solution (or the distilled hexafluoroacetone trihydrate distilled from the aqueous solution in the latter forms of the invention) is then admixed with concentrated sulfuric acid or oleum at a temperature of at least about 90° C. in an amount sufficient to produce a liquid containing sulfuric acid at a concentration of at least about 70% (by weight of $H_2SO_4$ divided by $H_2SO_4$ plus water) and a vapor consisting essentially of hexafluoroacetone and hexafluoroacetone monohydrate. The acid used in this step should be normally at least about 90% (basis $H_2SO_4$ as a fraction of $H_2SO_4$ plus water) and may exceed this concentration as in oleum. It is preferred not to use sulfur trioxide as such in this step, because of expense. So long as the sulfuric acid is sufficient in amount and concentration to produce a by-product acid containing at least about 70% $H_2SO_4$ and the temperature is at least about 90° C., the amount of hexafluoroacetone dissolved in the by-product acid will be low. The temperature is more preferably at least about 100° C., however, because still lower levels of residual hexafluoroacetone will be found at such reaction temperatures. The combined effects of different sulfuric acid concentrations and reaction temperatures can be illustrated by the following Table:

TABLE I

| Weight % $H_2SO_4$ | Solubility of 6FK (in weight %) | |
|---|---|---|
| | at 54° C. | at 100° C. |
| 90 | 0.2 | 0.03 |
| 93 | 0.15 | 0.01 |
| 98 | 0.01 | 0.006 |

Depending upon the sulfuric acid concentration (a function of the acid/aqueous solution ratios and concentrations) and the reaction temperature, the vapor produced will contain various proportions of hexafluoroacetone and hexafluoroacetone monohydrate, generally with the monohydrate accounting for a relatively minor proportion of the vapor on a volume, partial pressure or molar basis. This vapor should be scrubbed with liquid concentrated sulfuric acid at a flow rate sufficient to produce a purified hexafluoroacetone as a vapor of at least 99% purity. While sulfuric acid (e.g., 90-99% sulfuric acid, preferably 95-98% sulfuric acid) may be used for this scrubbing step and then fed into the aqueous solution for the admixing (dehydrating) step, it is not permissable to use oleum for the scrubbing step, since the product purified hexafluoroacetone would then be contaminated with sulfur trioxide.

There is a unique interaction between the nitrogen oxide impurities, the sulfur dioxide impurity, the water or aqueous solution in the absorption step and the sulfuric acid of the admixing (dehydrated) and scrubbing steps which enables the present process to operate without any neutralization. First the sulfur dioxide will either pass through the absorption step as a non-volatile or, commonly, will react with oxygen, nitrogen oxides and water to form sulfuric acid. Such sulfuric acid (or sulfate) will exist as a minor impurity in the aqueous solution and, during the dehydrating step, will merely be additive with the other sulfuric acid introduced or formed and represent no additional impurity in the by-product acid. The catalytic affect of $NO_x$ in the conversion of sulfur dioxide to sulfuric acid is known, and is used in the lead chamber sulfuric acid process. Nitrogen oxide impurities in the crude hexafluoroacetone will either pass through as non-volatiles or, more commonly, be absorbed to form nitric acid (assuming an excess of oxygen) or nitrous acid. While $NO_x$ gases will again be liberated during the dehydration step, they will be reabsorbed in the scrubbing step as nitrosyl sulfuric acid. This material ($NOHSO_4$) will be stable, and not revert to $NO_x$ gases so long as the sulfuric acid concentration of a by-product acid is at least 70%. Minor amounts of HF, if present, will also be dissolved in the by-product acid.

FIG. 1 illustrates, in partially schematic form, a preferred form for practicing the present invention.

An absorber 10, fitted preferably with a stirrer is fed by a crude hexafluoroacetone (6FK) stream 12 containing sulfur dioxide and nitrogen oxides as impurities, along with non-condensibles such as nitrogen, oxygen and carbon dioxide. Simultaneously, water is introduced via line 14. Absorber 10 is operated at about 50–60° C. and the ratio of streams 12 and 14 are adjusted to produce an aqueous solution of about 75 weight percent 6FK. Vent stream 16 (primarily non-condensibles) is removed from absorber 10, and optionally is scrubbed by incoming water in stream 14. Aqueous solution is removed from absorber 10 in stream 18.

The aqueous solution is fed in stream 18 (by pumping or metered gravity flow) to a reaction vessel 20, equipped with a stirrer. A scrubbing tower 22, having a packed section 24 starting above the base and ending near the top of the tower, is connected to the reactor 20 by an overflow line 26. Concentrated sulfuric acid is fed over the top of packed section 24 in stream 28 to absorb 6FK monohydrate from the vapor mixture produced in reactor 20. Liquid dripping from packed section 24 collects at the base of absorption tower 22 and is pumped at a metered flow rate through recirculating line 30 back into stream 28. The metered rate in line 30 is smaller than the flow in stream 28, such that a portion of the liquid overflows through overflow line 26 into reactor 20. Because this overflowing liquid contains 6FK monohydrate, which has a 40° C. melting point, overflow line 26 should be warmed to maintain a temperature of 50°–60° C. The tower 26 will be at approximately the temperature of incoming acid in stream 28

(15°–25° C.). Make-up sulfuric acid 32 is fed into stream 28.

Reactor 20 is heated (as by steam-jacketing) to maintain a temperature above 90° C. (e.g. 100°–110° C.) which is limited only by the desire to avoid sulfuric acid boiling (which is a function of concentration and pressure). By-product acid, containing water and impurities such as nitrosyl sulfuric acid, is removed from reactor 20 in stream 36. By adjusting the concentration and amount of make-up sulfuric acid 32 relative to aqueous solution (stream 18), the by-product acid can be made to have a sulfuric acid concentration of above 70%, preferably 80–95%. With these two conditions (reactor temperature and by-product acid concentration) properly controlled, the 6FK concentration in stream 36 will be very low (see Table 1, above). Sufficient flux of sulfuric acid fed in stream 28 through tower 22 will produce purified anhydrous 6FK (removed in stream 34) of high purity.

Several modifications are contemplated in the process as illustrated in FIG. 1. If impurities in crude 6FK stream 12 (e.g., HFTA) form a separate phase in the aqueous solution, then stream 18 would be fed to a phase separation device and only the aqueous phase fed to reactor 20. If certain impurities (e.g., carbon dioxide) remain in the aqueous solution, it may be refluxed (after phase separation, if used) to disengage such impurities to the extent possible, before introduction into reactor 20. Tower 22 may be split into a packed tower and a receiving vessel, with overflow lines 26 and recirculating line 30 connected to the receiving vessel. Absorber 10 may be operated as an absorption column with stream 14 feeding water near the top, streams 18 removing aqueous solution from the bottom, stream 12 feeding crude 6FK just below the feedpoint of stream 14.

The present invention is illustrated by the following Examples, which are intended to illustrate, but not limit the present invention.

EXAMPLE 1

A crude hexafluoroacetone stream was produced by $NO_x$ oxidation of hexafluorothioacetone (HFTA) in accordance with U.S. Pat. No. 4,337,361. The crude hexafluoroacetone was absorbed in a recycled water scrubber operating between 50° and 60° C. to produce an aqueous solution having the following composition, by weight percent:

Nitric Acid—2.7%, Sulfuric Acid—6.2%, Hexafluoroacetone (6FK)—58.8%, HFTA—3.7%, Water—28.6%.

The liquid was permitted to stand, with two phases forming; and the lower HFTA phase was removed, producing a composition having: Nitric Acid—2.8%, Sulfuric Acid —6.4%, 6FK—61%, Water—29.8%. This product was fed to a regenerator along with 171 grams of 100% sulfuric acid, which acid was fed through a recirculating absorption tower as illustrated by elements 22, 26, 28, 30 and 32 in FIG. 1. While 1.595 moles (156.3 g) sulfuric acid would be needed by subtracting the moles sulfuric acid present from the moles water present, 171 g (1.745 moles) was used, to insure an excess and to consider the possibility that the nitric acid would consume additional sulfuric acid. The regenerator was operated at 110° C. (temperature of the pot 20 and the by-product acid stream 36), and the vapor recovered (stream 34) contained 61 g pure hexafluoroacetone for a yield of approximately 100%.

EXAMPLE 2

Following the procedure of Example 1, crude 6FK was absorbed in water such that, after phase separation to remove carried over the HFTA, the composition was 3.1% nitric acid, 7.1% sulfuric acid, 80% hexafluoroacetone and 9.8% water. Aqueous sodium hydroxide (15.5 g of 50 weight percent NaOH) was added to neutralize the free nitric and sulfuric acid, and the product was filtered to remove essentially all of the sodium nitrate and sodium sulfate. The filtrate was then flash evaporated to dryness to yield 160 g of hexafluoroacetone trihydrate, with a boiling point of 106° C. The condensate analyzed as 75.45 weight percent hexafluoroacetone by potentiometric titration. Since 177 g of 96 weight percent of sulfuric acid per 100 parts of this solution would represent 1 mole of $H_2SO_4$ per mole of water, 200 g of 96 weight percent sulfuric acid was fed (to insure an excess) to the decomposer. Operating at 105° C., the hexafluoroacetone recovered was essentially pure and in quantitative yield.

EXAMPLE 3

The material present in Example 2, after sodium hydroxide addition but before supplemental water, was boiled under reflux to yield 15.5 g of dry hexafluoroacetone, which was condensed using dry ice. This indicates that an aqueous solution having more than 75.45% hexafluoroacetone (basis hexafluoroacetone plus water) on a weight basis will, when heated, decompose to form hexafluoroacetone itself, which has a boiling point of −28° C. at one atmosphere pressure.

What is claimed is:

1. A process for the purification of crude hexafluoroacetone, containing as impurities nitrogen oxides and sulfur dioxide, which process comprises the steps:
   (a) admixing the crude hexafluoroacetone with sufficient water at a temperature between about 40° C. and about 70° C. to produce an aqueous solution containing between about 70 and about 85 weight percent hexafluoroacetone, based upon weight of hexafluoroacetone and water,
   (b) admixing the aqueous solution with concentrated sulfuric acid or oleum at a temperature of at least about 90° C. in an amount sufficient to produce a liquid containing sulfuric acid at a concentration of at least about 70% (by weight of $H_2SO_4$ divided by $H_2SO_4$ plus water) and a vapor consisting essentially of hexafluoroacetone and hexafluoroacetone monohydrate, and
   (c) scrubbing said vapor consisting essentially of hexafluoroacetone and hexafluoroacetone monohydrate with liquid concentrated sulfuric acid at a flow rate sufficient to produce purified anhydrous hexafluoroacetone as a vapor of at least 99% purity.

2. The process of claim 1 wherein said crude hexafluoroacetone has been produced by the oxidation with nitrogen oxides of hexafluorothioacetone dimer.

3. The process of claim 1 wherein step (a) is conducted at a temperature between about 50° C. and about 60° C.

4. The process of claim 1 wherein sufficient water is used in step (a) to produce an aqueous solution containing between about 72 and about 82 weight percent hexafluoroacetone, based upon hexafluoroacetone and water.

5. The process of claim 4 wherein the aqueous solution contains about 72 to about 76 weight percent hexafluoroacetone and wherein hexafluoroacetone trihydrate is distilled from said aqueous solution formed in step (a) and is admixed with sulfuric acid or oleum in step (b).

6. The process of claim 1 wherein step (b) is performed at a temperature of at least about 100° C.

7. The process of claim 1 wherein sufficiently concentrated sulfuric acid or oleum is used in sufficient amount in step (b) to produce a liquid containing a concentration between about 80 and about 95% (by weight of $H_2SO_4$, divided by $H_2SO_4$ plus water).

8. The process of claim 1 wherein the concentrated sulfuric acid or oleum used contains between about 0.8 and about 1.4 moles $H_2SO_4$ per total mole of water in the sulfuric acid and in the aqueous solution with which it is admixed in step (b).

9. The process of claim 8 wherein the concentrated sulfuric acid or oleum used contains between about 1.0 and about 1.2 moles $H_2SO_4$ per total mole of water in the sulfuric acid and in the aqueous solution with which it is admixed in step (b).

* * * * *